US00PP09976P

United States Patent [19]

Porter

[11] Patent Number: Plant 9,976

[45] Date of Patent: Jul. 22, 1997

[54] BERMUDAGRASS PLANT TDS-BM1

[76] Inventor: William Emme Porter, 5200 N. Hwy. 85, Las Cruces, N. Mex. 88005

[21] Appl. No.: 506,921

[22] Filed: Jul. 26, 1995

[51] Int. Cl.[6] ..... A01H 5/00

[52] U.S. Cl. ..... Plt./90

[58] Field of Search ..... 800/200, DIG. 55; 47/58; Plt./90

[56] References Cited

PUBLICATIONS

Dudeck, NTEP Bermudagrass Trial in North Florida. In:Turfgrass Research in Florida, A Technical Report. Ed. Cisnar. pp. 27–53. 1995.

Morton et al. 1994 Update for the National Turfgrass Evaluation Program (NTEP) Trial at TAES–Dallas: 1992 Bermudagrass Trial. Texas Turfgrass Research Report. pp. 13–19. 1994.

Morton et al. Performance of Three Warm–Season Turfgrass Genera Cultured in Shade II. *Cynodon dactylon*. Texas Turfgrass Research Report. pp. 24–26. 1994.

Marcum et al. Salinity Tolerances of Selected Bermudagrass and Zoysiagrass Genotypes. Texas Turf Research Report. pp. 105–107. 1993.

National Bermudagrass Test—1992. National Turfgrass Evaluation Program. pp. 1–30. 1992.

*Primary Examiner*—James R. Feyrer
*Assistant Examiner*—Melissa L. Kimball
*Attorney, Agent, or Firm*—V. G. Lehman

[57] ABSTRACT

An asexually reproduced variety of bermudagrass with a unique combination of characters including good turf quality, white anthers, fine textured leaf blade, high culm production, and a distinct DNA fingerprint.

2 Drawing Sheets

BACKGROUND OF THE INVENTION

'TDS-BM1' is a new and distinct variety of bermudagrass (*Cynodon dactylon*) discovered by me under a heavily trafficked cultivated, mowed turf in a home lawn in Las Cruces, N. Mex. TDS-BM1 spreads rapidly by both stolons and rhizomes. TDS-BM1 is suitable for use as turf on golf course fairways, sports fields, home lawns, industrial sites, and other sites wherever bermudagrasses are adapted. TDS-BM1 was identified for its diminutive growth pattern, finer leaf texture, and persistence under heavy traffic as compared to surrounding bermudagrass. TDS-BM1 was asexually propagated by me in Las Cruces, N. Mex. by cutting of stolons and rhizomes, rooting them in soil, and planting of the rooted stolons and rhizomes to provide planting stock for studying performance and for comparisons with commercial varieties. TDS-BM1 remained stable in both performance and morphological characters after propagation.

A bermudagrass designated C84-135 was disclosed in U.S. Pat. No. P.P. 6,278, issued on Sep. 6, 1988. A bermudagrass designated CT-2 was disclosed in U.S. Pat. No. P.P. 6,841, issued on Jun. 6, 1989. A bermudagrass designated World Feeder was disclosed in U.S. Pat. No. P.P. 7,081, issued on Dec. 19, 1989. A bermudagrass designated Midlawn was disclosed in U.S. Pat. No. P.P. 8,162, issued on Feb. 23, 1993. Another bermudagrass designated Midfield was disclosed in U.S. Pat. No. P.P. 8,168, issued on Mar. 2, 1993.

SUMMARY OF THE INVENTION

TDS-BM1 is distinguished from other varieties of bermudagrass by the combination of characters of turf performance, shade tolerance, white anthers, leaf texture, culm production, and a distinct DNA fingerprint.

BRIEF DESCRIPTIONS OF THE ILLUSTRATIONS

FIG. 1–3 are DNA fingerprints of bermudagrass varieties. The RAPD analysis illustrate TDS-BM1 is different from both Tifgreen and Tifway.

COMPLETE DESCRIPTION OF THE VARIETY

TDS-BM1 is a new and distinct variety of bermudagrass that spreads by stolons and rhizomes. TDS-BM1 is a bermudagrass similar in appearance to Tifgreen and Tifway. TDS-BM1 had a mean stolon internode length of 33.3 mm for nodes 2 through 4 with Tifgreen having a mean of 35.8 mm in measurements on greenhouse grown plants. The leaf blade width of the third youngest leaf on TDS-BM1 was 1.99 mm with Tifgreen having a mean of 2.25 mm. The diameter of the third node on a vegetative stolon of TDS-BM1 was 0.87 with Tifgreen having a mean of 0.99.

In trials in Gainseville, Fla., TDS-BM1 was reported as having high seasonal turf quality in 1993 with a mean of 6.87, and was statistically higher in quality than Tifgreen (Table 1). TDS-BM1 was also higher in quality than Tifgreen in 1994 in Florida trials (Table 2). In the 1992 and 1993 NTEP trials in Texas, TDS-BM1 ranked second and first in quality of 26 entries. In color ratings of vegetative bermudagrasses, TDS-BM1 is not statistically different from Tifgreen or Tifway (Tables 3,4). In addition, in the 1992 and 1993 NTEP Trials, TDS-BM1 had a mean color rating of 6.7 in both years. TDS-BM1 has a fine textured leaf blade compared to Midfield, Midlawn, and Midiron (Table 5). In the 1992 NTEP trials (TAES-Dallas), TDS-BM1 was reported to have a statistically finer leaf blade than Midlawn, Midiron, Midfield, Texturf 10, and STF-1 in both 1992 and 1993.

TDS-BM1 has a rapid rate of spread (Table 6). Under shaded conditions, TDS-BM1 maintains higher percent plot cover compared to Tifgreen (Table 7,8). In trials in Mississippi, TDS-BM1 was statistically earlier in greenup than 16 entries in the National Bermudagrass Trial for 1993 and 1994 (Table 9). In the 1993 NTEP report from Mississippi, TDS-BM1 reported the second highest spring greenup rate of 26 varieties at 11 different locations.

TDS-BM1 has the highest number of seedheads in the Florida trials in 1993 (Table 1). TDS-BM1 had the highest seedhead production in trials in Dallas (Table 10–12). TDS-BM1 has white anthers, similar to Tifgreen and Midfield (Table 13).

TDS-BM1 showed lower salt injury than Midiron, Texturf 10, and STF-1 in evaluations of percent shoot salt injury at Texas A&M -Dallas, of the 1992 National Turfgrass Evaluation Program (Table 14). TDS-BM1 showed higher susceptibility to pink snow mold than Midfield, Midiron, or Midlawn (Table 15).

Figure 3:
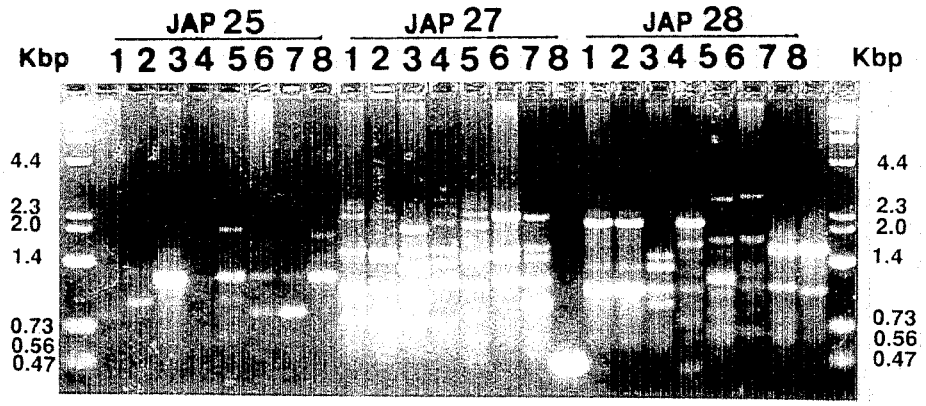
Figure 4:
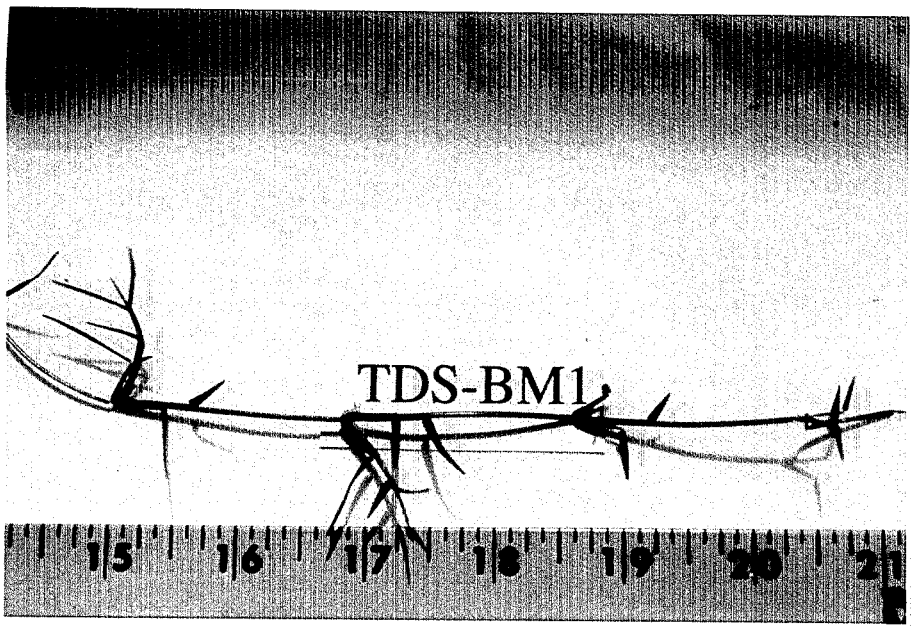
FIG. 4 is a photograph of a stolon of TDS-BM1.

TDS-BM1 shows a distinctly different DNA from Tifgreen using RAPD analysis using a single primer of an arbitral oligonucleotide referred to as JAP 29 (FIG. 1) of JAP 26 (FIG. 2). Both TDS-BM1 and Tifgreen may be distinguished from Tifway using a single primer of an arbitral oligonucleotide referred to as JAP 26 (FIG. 2) and JAP 25 or JAP 27 (FIG. 3).

TABLE 1

Seasonal and average estimates of bermudagrass turf quality and seed head production during the third growing season in 1993 at Gainesville, FL. (Partial data set)

| | Quality[1] | | | | |
|---|---|---|---|---|---|
| | May–June | July–Aug. | Sept.–Nov. | Average | Seed Heads[2] |
| FHB-135 | 6.6 | 7.1 | 6.7 | 6.90 a* | 1.0 g |
| TDS-BM1 | 7.1 | 6.9 | 7.1 | 6.87 a | 5.1 ab |
| Tifway | 6.6 | 6.6 | 6.7 | 6.49 ab | 1.6 e–g |
| Midiron | 6.0 | 6.1 | 7.3 | 6.36 a–c | 3.3 c |
| Sultan | 6.0 | 6.1 | 6.1 | 6.15 b–d | 2.1 d–g |
| Texturf 10 | 6.0 | 6.0 | 6.1 | 6.10 b–e | 1.6 e–g |
| Tifgreen | 6.6 | 5.8 | 6.3 | 6.03 b–f | 4.4 b |
| Midfield | 6.1 | 5.8 | 6.2 | 6.03 b–f | 2.0 d–g |
| Sonesta | 6.4 | 6.0 | 5.3 | 5.80 b–g | 2.0 d–g |
| MSD | 0.8 | 0.6 | 1.3 | 0.70 | 1.1 |

[1]Quality visually rated 1 to 9 where 9 equaled best turf quality.
[2]Seed heads visually rated 1 to 9 where 1 equaled no seed heads and 9 equaled many seedheads. Eight ratings throughout the season were averaged.
*Means within columns with the same letter are not significantly different (P = 0.05) using Waller-Duncan k-ratio t-test.
MSD is the minimum significant difference between any two means within columns which must be exceeded to be significantly different (P = 0.05) using Waller-Duncan k-ratio t-test.
Dudeck, A. E. 1995. NTEP bermudagrass trials in North Florida. In Turfgrass Research in Florida, ed. J. L. Cisar. University of Florida, Institute of Food and Agricultural Sciences, Florida Agricultural Experiment Station, Gainseville, FL.

TABLE 2

Seasonal and average estimates of bermudagrass turf quality and seed head production during the third growing season in 1994 at Gainesville, FL (data presented for vegetatively planted varieties only).

| | Quality[1] | | | | |
|---|---|---|---|---|---|
| | Mar–May | June–Aug. | Sept.–Dec. | Average | Seed Heads[2] |
| FHB-240 | 8.2 | 7.4 | 7.0 | 7.53 a* | 1.73 g |
| TDS-BM1 | 7.9 | 7.3 | 7.1 | 7.45 ab | 1.40 g |
| Tifway | 6.9 | 7.8 | 7.4 | 7.35 a–c | 1.00 g |
| FHB-227 | 7.8 | 7.1 | 7.1 | 7.35 a–c | 1.47 g |
| FHB-285 | 6.8 | 7.8 | 7.4 | 7.31 a–c | 1.00 g |
| FHB-281 | 6.4 | 7.0 | 7.4 | 6.92 b–d | 1.20 g |

TABLE 2-continued

Seasonal and average estimates of bermudagrass turf quality and seed head production during the third growing season in 1994 at Gainesville, FL (data presented for vegetatively planted varieties only).

| | Quality[1] | | | | |
|---|---|---|---|---|---|
| | Mar–May | June–Aug. | Sept.–Dec. | Average | Seed Heads[2] |
| Texturf 10 | 7.2 | 6.8 | 6.6 | 6.86 cd | 1.20 g |
| Midiron | 6.8 | 6.4 | 6.7 | 6.67 de | 1.00 g |
| Tifgreen | 6.3 | 6.9 | 6.6 | 6.57 de | 1.53 g |
| MSD | 0.7 | 0.7 | 0.7 | 0.57 | 0.87 |

[1]Quality visually rated 1 to where 9 equaled best turf quality.
[2]Seed heads visually rated 1 to 9 where 1 equaled no seed heads and 9 equaled many seedheads. Thirteen ratings throughout the season were averaged.
*Means within columns with the same letter are not significantly different (P = 0.05) using Waller-Duncan k-ratio t-test.
MSD is the minimum significant difference between any two means within columns which must be exceeded to be significantly different (P = 0.05) using Waller-Duncan k-ratio t-test.
Dudeck, A. E. 1995. NTEP bermudagrass trials in North Florida. In Turfgrass Research in Florida, ed. J. L. Cisar. University of Florida, Institute of Food and Agricultural Sciences, Florida Agricultural Experiment Station, Gainseville, FL.

TABLE 3

Color[1] quality of 1992 NTEP bermudagrasses - TAES-Dallas during 1992–3. (Vegetative entries only).

| | Date | | | | | | |
|---|---|---|---|---|---|---|---|
| Entry | 26 Sept 92 | 20 Jan 93 | 24 Feb 93 | 16 Apr 93 | 26 May 93 | 22 Jun 93 | TPI |
| AZ common | 4.7 a | 2.0 | 2.3 a | 5.0 | 7.0 | 7.7 | 2 |
| FHB-135 | 3.0 | 3.0 | 2.0 | 7.3 a | 8.0 | 7.3 | 1 |
| Midfield | 3.7 | 4.0 a | 3.0 a | 8.0 a | 9.0 a | 8.7 a | 5 |
| Midiron | 3.7 | 4.7 a | 2.3 a | 7.3 a | 9.0 a | 8.3 a | 5 |
| Midlawn | 4.7 a | 4.0 a | 3.0 a | 7.7 a | 9.0 a | 7.7 | 5 |
| STF-1 | 4.0 a | 4.3 a | 3.0 a | 8.0 a | 8.0 | 8.3 a | 5 |
| TDS-BM1 | 3.7 | 4.0 a | 3.0 a | 8.0 a | 8.3 | 8.7 a | 4 |
| Texturf 10 | 4.3 a | 2.7 | 3.0 a | 7.7 a | 8.0 | 7.7 | 3 |
| Tifgreen | 3.0 | 4.7 a | 3.0 a | 8.3 a | 8.0 | 8.3 a | 4 |
| Tifway | 3.7 | 4.3 a | 3.0 a | 7.7 a | 8.0 | 8.0 a | 4 |
| MSD entry[2] | 1.1 | 0.8 | 0.7 | 1.4 | 0.7 | 0.8 | |

[1]Color quality was estimated for a range from 1 to 9, where 9 is the ideal green turf color, and 5 is the minimum acceptable green turf color.
[2]MSD entry = minimum significant difference between entry means, which is based on the Waller-Duncan K-ratio t-test (k-ratio = 100). Means in the top statistical group are indicated by an 'a'.
Morton, S. J. and M. C. Engelke. 1993. Bermudagrass entries in the National Turfgrass Evaluation program Trial at Dallas. PR. 5111. In Texas Turfgrass Research Reports, ed. P. F. Colbaugh and S. P. Metz. Texas A & M University System, College Station, TX, 77843.

TABLE 4

Color[1] ratings during 1993–4 for the 1992 NTEP bermudagrass trial planted at TAES-Dallas. (Vegetative entries only).

| | 1993 | | | | | 1994 |
|---|---|---|---|---|---|---|
| Entry | 28 July | 31 Aug | 28 Sept | 27 Oct | 18 Feb | TPI |
| AZ common | 6.0 a | 7.0 | 6.0 | 6.0 | 1.0 | 1 |
| FHB-135 | 6.3 a | 6.0 | 4.0 | 5.7 | 1.0 | 1 |
| Midfield | 4.3 | 8.3 | 5.0 | 5.7 | 1.7 | 0 |
| Midiron | 6.0 a | 7.0 | 4.7 | 4.0 | 1.7 | 1 |
| Midlawn | 5.0 | 7.0 | 5.7 | 5.7 | 1.7 | 0 |
| STF-1 | 6.0 a | 7.7 | 5.3 | 5.3 | 2.0 a | 2 |
| TDS-BM1 | 6.0 a | 5.7 | 5.0 | 5.7 | 2.0 a | 2 |

TABLE 4-continued

Color[1] ratings during 1993–4 for the 1992 NTEP bermudagrass trial planted at TAES-Dallas. (Vegetative entries only).

| | 1993 | | | | | 1994 |
|---|---|---|---|---|---|---|
| Entry | 28 July | 31 Aug | 28 Sept | 27 Oct | 18 Feb | TPI |
| Texturf 10 | 6.3 a | 6.7 | 5.7 | 6.0 | 1.7 | 1 |
| Tifgreen | 5.0 | 6.3 | 5.0 | 5.7 | 1.7 | 0 |
| Tifway | 4.7 | 6.7 | 5.7 | 6.0 | 2.7 a | 1 |
| MSD entry[2] | 0.9 | ns | ns | ns | 1.0 | |

[1]Color ratings were estimated, on a scale of 1 to 9, where 9 represented the darkest green, and 5 was the minimum acceptable color.

[2]MSD entry is the minimum significant difference between the entry means, which is based on the Waller-Duncan k-ratio t test (k-ratio = 100). 'ns' indicates that no statistical difference occurred between entry means. Means in the top statistical group are indicated by 'a'.

Morton, S. J. and M. C. Engelke. 1994. 1994 Update for the National Turfgrass Evaluation Program (NTEP) Trial at TAES-Dallas: 1992 Bermudagrass Trial. PR. 5240. In Texas Turfgrass Research Reports, ed. M. C. Engelke. Texas A & M University System, College Station, TX, 77843.

TABLE 5

Leaf texture on September 26, 1992 of bermudagrasses in the 1992 NTEP planted at TAES-Dallas. (Vegetative entries only).

| Entry | Leaf Texture |
|---|---|
| AZ common | Medium |
| FHB-135 | Fine |
| Midfield | Coarse |
| Midiron | Medium |
| Midlawn | Medium |
| STF-1 | Medium fine |
| TDS-BM1 | Fine |
| Texturf 10 | Medium fine |
| Tifgreen | Fine |
| Tifway | Fine |

Texture was estimated on a scale of 1 to 3, where 3 was the finest leaf blade and 1 was the coarsest leaf blade.

Morton, S. J. and M. C. Engelke. 1994. Bermudagrass entries in the National Turfgrass Evaluation program Trial at Dallas. PR. 5111. In Texas Turfgrass Research Reports, ed. P. F. Colbaugh and S. Metz. Texas A & M University System, College Station, TX, 77843.

TABLE 6

Turf cover establishment by 1992 NTEP bermudagrasses planted on July 14, 1992 at TAES-Dallas.

| | Percent turf cover[1] Date | | | | | | | |
|---|---|---|---|---|---|---|---|---|
| Entry | 9 Aug | 26 Aug | 26 Sep | 23 Oct | 24 Feb | 26 May | 22 Jun | TPI[2] |
| AZ Com | 23 | 40 | 98 a | 99 a | 98 | 92 a | 92 | 4 |
| FHB-135 | 17 | 19 | 73 | 77 | 80 | 73 | 89 | 1 |
| Midfield | 26 | 43 | 98 a | 99 a | 99 | 96 a | 96 a | 5 |
| Midiron | 15 | 23 | 83 | 93 a | 97 | 96 a | 95 a | 4 |
| Midlawn | 26 | 45 | 99 a | 99 a | 99 | 96 a | 95 a | 5 |
| STF-1 | 16 | 28 | 90 a | 99 a | 99 | 96 a | 96 a | 5 |
| TDS-BM1 | 24 | 53 a | 93 a | 88 a | 87 | 91 a | 94 a | 6 |
| Texturf 10 | 18 | 28 | 95 a | 98 a | 99 | 96 a | 96 a | 5 |
| Tifgreen | 25 | 42 | 99 a | 99 a | 99 | 96 a | 96 a | 5 |

TABLE 6-continued

Turf cover establishment by 1992 NTEP bermudagrasses planted on July 14, 1992 at TAES-Dallas.

| | Percent turf cover[1] Date | | | | | | | |
|---|---|---|---|---|---|---|---|---|
| Entry | 9 Aug | 26 Aug | 26 Sep | 23 Oct | 24 Feb | 26 May | 22 Jun | TPI[2] |
| Tifway | 13 | 23 | 80 | 86 a | 88 | 89 a | 93 a | 4 |
| MSD Entry[3] | 18 | 22 | 14 | 20 | ns | 8 | 83 | |

[1]Turf cover is noted as the percent of the plot coverage for each date.

[2]TPI = Turf Performance Index, which is the total number of times an entry occurred in the top statistical group.

MSD entry = minimum significant difference between entry means, which is based on the [3]Waller-Duncan k-ratio t-test (k-ratio = 100). NS = no significant difference occurred between entry means. Means in the top statistical group are indicated by an 'a'.

Morton, S. J. and M. C. Engelke. 1993. Bermudagrass entries in the National Turfgrass Evaluation program Trial at Dallas. PR. 5111. In Texas Turfgrass Research Reports, ed. P. F. Colbaugh and S. F. Metz. Texas A & M University System, College Station, TX, 77843.

TABLE 7

Turf cover, as percentage of the plot that has turf ground cover, for bermudagrasses of the 1992 NTEP planted in 90% shade at TAES-Dallas.

| | Percent Turf Cover Date | | | |
|---|---|---|---|---|
| Entry | 11 Nov 93 | 21 Dec 93 | 16 Mar 94 | TPI |
| AZ common | 15.0 | 15.0 | 9.7 | 0 |
| FHB-135 | 35.0 a | 47.7 a | 10.7 | 2 |
| Midfield | 31.7 a | 25.0 | 12.3 | 1 |
| Midiron | 28.3 | 41.7 a | 11.7 | 1 |
| Midlawn | 31.7 a | 48.3 a | 11.7 | 2 |
| STF-1 | 35.0 a | 36.7 | 10.0 | 1 |
| TDS-BM1 | 51.7 a | 51.7 a | 15.0 a | 3 |
| Texturf 10 | 23.3 | 38.3 a | 7.3 | 1 |
| Tifgreen | 28.3 | 30.0 | 9.0 | 1 |
| Tifway | 55.0 a | 58.3 a | 12.3 | 2 |
| MSD entry[1] | 1.8 | 1.2 | 1.6 | |

[1]MSD entry is the minimum significant difference between the entry means, which is based on the Waller-Duncan k-ratio t test (k-ratio = 100). 'ns' indicates that no statistical difference occurred between entry means. Means in the top statistical group are indicated by 'a'.

Morton, S. J. and M. C. Engelke. 1994. Performance of three warm-season turfgrass genera cultured in shade II. *Cynodon dactylon*. PR. 5243. In Texas Turfgrass Research Reports, ed. M. C. Engelke. Texas A & M University System, College Station, TX, 77843.

TABLE 8

Turf cover, as percentage of the plot that has turf ground cover, for bermudagrasses of the 1992 NTEP planed in 90% shade at TAES-Dallas.

| | Percent green turf cover 1993 | | | | |
|---|---|---|---|---|---|
| Vegetative Entry | 7 May | 8 June | 9 July | 3 Aug | TPI[1] |
| AZ Common | 43 | 18 | 33 | 33 | — |
| FHB-135 | 57 a | 53 a | 72 a | 53 a | 4 |
| Midfield | 50 | 47 a | 62 | 48 | 1 |
| Midiron | 50 | 50 a | 58 | 45 | 1 |
| Midlawn | 60 a | 43 a | 70 a | 50 | 3 |
| STF-1 | 53 a | 33 | 52 | 43 | 1 |
| TDS-BM1 | 63 a | 55 a | 80 a | 63 a | 4 |
| Texturf 10 | 50 | 38 | 60 | 47 | — |
| Tifgreen | 53 a | 30 | 55 | 42 | 1 |

TABLE 8-continued

Turf cover, as percentage of the plot that has turf ground cover, for bermudagrasses of the 1992 NTEP planed in 90% shade at TAES-Dallas.

| | Percent green turf cover 1993 | | | | |
|---|---|---|---|---|---|
| Vegetative Entry | 7 May | 8 June | 9 July | 3 Aug | TPI[1] |
| Tifway | 63 a | 55 a | 73 a | 53 a | 4 |
| MSD entry[2] | 13 | 14 | 14 | 12 | |

[1]TPI = turf performance index, which was the number of times an entry occurred in the top statistical group.

[2]MSD entry - minimum significant difference between entry means for comparison within a column, which is based on the Waller-Duncan k-ratio t-test (K-ratio = 100). Means in the top statistical group are designated by an 'a'.

Morton, S. J. and M. C. Engelke. 1993. Performance of three warm-season turfgrass genera cultured in shade. II. *Cynodon dactylon*. In Texas Turfgrass Research Reports, ed. P. F. Colbaugh and S. F. Metz. PR-5138. Texas A & M University System, College Station, TX, 77843.

TABLE 9

Spring green-up ratings of the National Bermudagrass Test - 1992. (Mississippi State University).

| Entry | 1993 | 1994 | 2 year average |
|---|---|---|---|
| Midiron | 6.4[1] | 5.7 | 6.1 |
| TDS-BM1 | 6.4 | 5.7 | 6.0 |
| Tifgreen | 6.6 | 5.2 | 5.9 |
| Midfield | 6.7 | 5.0 | 5.9 |
| Tifdwarf | 6.3 | 4.9 | 5.6 |
| Tifway | 6.3 | 4.8 | 5.6 |
| Guymon | 5.7 | 5.1 | 5.4 |
| Texturf 10 | 5.9 | 4.9 | 5.4 |
| STF-1 | 6.1 | 4.3 | 5.2 |
| ZPS-B1 | 5.3 | 5.0 | 5.1 |
| Midlawn | 5.7 | 4.4 | 5.1 |
| J-27 | 4.9 | 5.2 | 5.1 |
| FHB-135 | 5.9 | 3.8 | 4.8 |
| OKS 91-11 | 4.9 | 4.6 | 4.7 |
| MSB-40 | 5.2 | 4.1 | 4.6 |
| 90173 | 3.5 | 5.6 | 4.5 |
| AZ Com.-veg | 4.7 | 4.7 | 4.1 |
| J-192 | 4.0 | 4.2 | 4.1 |
| FMC 5-91 | 3.1 | 4.9 | 4.0 |
| FMC 6-91 | 2.7 | 4.9 | 3.8 |
| FMC 2-90 | 2.9 | 4.7 | 3.8 |
| OKS 91-1 | 2.7 | 4.6 | 3.6 |
| Cheyenne | 2.4 | 4.7 | 3.6 |
| Sundevil | 2.3 | 4.8 | 3.5 |
| Sonesta | 2.2 | 4.8 | 3.5 |
| FMC 3-91 | 2.1 | 4.8 | 3.4 |
| AZ Com.-seed | 2.2 | 4.3 | 3.4 |
| Sahara | 2.1 | 4.6 | 3.3 |
| FMC 1-90 | 1.8 | 4.7 | 3.3 |
| Mean | 4.4 | 4.8 | 4.6 |
| LSD (0.05) | 0.7 | 0.7 | 1.2 |

[1]9 = completely green, 1 = brown

Philley, H. W., J. V. Krans, J. M. Goatley, Jr., and V. L. Maddox. 1994. Update on the National Bermudagrass Tests-1992 at MSU. In Mississippi Turfgrass Research Progress Report - 1994. Bulletin 274. Miss Agric & Forestry Exp St. Mississippi State, MS 39762.

TABLE 10

Seedhead production during 1993 for the 1992 NTEP bermudagrass trial planted at TAES-Dallas. (Vegetative entries only).

| | Seedhead Density[1] Date | | |
|---|---|---|---|
| Entry | 8 Jun 93 | 23 Aug 93 | Mean |
| AZ common | 1.0 | 1.3 | 1.2 |
| FHB-135 | 0.0 | 1.0 | 0.5 |
| Midfield | 2.7 | 0.0 | 1.3 |
| Midiron | 2.7 | 0.3 | 1.5 |
| Midlawn | 1.7 | 0.3 | 1.0 |
| STF-1 | 5.3 | 0.3 | 2.8 |
| TDS-BM1 | 7.3 a | 2.7 a | 5.0 a |
| Texturf 10 | 1.7 | 0.7 | 1.2 |
| Tifgreen | 4.7 | 0.7 | 2.7 |
| Tifway | 1.7 | 0.3 | 1.0 |
| MSD entry[2] | 1.8 | 1.2 | 1.6 |

[1]Seedhead density estimated on a scale of 1–9, where 9 represents highest seedhead density.

[2]MSD entry is the minimum significant difference between the entry means, which is based on the Waller-Duncan k-ratio t test (k-ratio = 100). 'ns' indicates that no statistical difference occurred between entry means. Means in top statistical group are indicated by 'a'.

Morton, S. J. and M. C. Engelke. 1994. 1994 Update for the National Turfgrass Evaluation Program (NTEP) Trial at TAES-Dallas: 1992 Bermudagrass Trial. PR. 5240. In Texas Turfgrass Research Reports, ed. M. C. Engelke. Texas A & M University System, College Station, TX, 77843.

TABLE 11

Seedhead production during 1993 for the 1992 NTEP bermudagrass trial planted at TAES-Dallas. (Vegetative entries only).

| | Seedheads/sq. inch Date | | |
|---|---|---|---|
| Entry | 6 July 93 | 4 Nov 93 | Mean |
| AZ common | 0 | 7 | 4 |
| FHB-135 | 3 | 0 | 2 |
| Midfield | 11 | 0 | 6 |
| Midiron | 2 | 1 | 1 |
| Midlawn | 0 | 0 | 0 |
| STF-1 | 7 | 26 a | 16 a |
| TDS-BM1 | 46 a | 0 | 23 a |
| Texturf 10 | 1 | 6 | 4 |
| Tifgreen | 13 | 0 | 7 |
| Tifway | 0 | 0 | 0 |
| MSD entry[1] | 9 | 12 | 13 |

[1]MSD entry is the minimum significant difference between the entry means, which is based on the Waller-Duncan k-ratio t test (k-ratio = 100). 'ns' indicates that no statistical difference occurred between entry means. Means in the top statistical group are indicated by 'a'.

Morton, S. J. and M. C. Engelke. 1994. 1994 Update for the National Turfgrass Evaluation Program (NTEP) Trial at TAES-Dallas: 1992 Bermudagrass Trial. PR. 5240. In Texas Turfgrass Research Reports, ed. M. C. Engelke. Texas A & M University System, College Station, TX, 77843.

TABLE 12

Culm production on June 8 (visual) and July 6, 1993 (count) by 1992 NTEP bermudagrasses planted at TAES-Dallas. (Vegetative entries only).

| Entry | 8 June Visual[1] | 6 July Count[1] |
|---|---|---|
| Midfield | 2.7 d–g* | 11.3 bc |
| Midlawn | 1.7 e–h | 0.0 d |
| Tifgreen | 4.7 bc | 1.3 d |
| STF-1 | 5.3 b | 6.7 b–d |
| Texturf 10 | 1.7 e–h | 0.0 d |
| Midiron | 2.7 d–g | 2.0 d |

TABLE 12-continued

Culm production on June 8 (visual) and July 6, 1993 (count) by 1992 NTEP bermudagrasses planted at TAES-Dallas. (Vegetative entries only).

| Entry | 8 June Visual[1] | 6 July Count[1] |
|---|---|---|
| TDS-BM1 | 7.3 a | 46.3 a |
| Tifway | 1.7 e–h | 13.3 b |
| AZ common | 1.0 gh | 0.3 d |
| FHB-135 | 0.0 h | 3.0 cd |

[1]Visual = 1–9, where 9 = most seed heads. Count = number/80.6 cm sq.
*Means with the same letter were not significantly different, based on the Waller-Duncan k-ratio t-test (k-ratio = 100).
Morton, S. J. and M. C. Engelke. 1993. Bermudagrass entries in the National Turfgrass Evaluation program Trial at Dallas. PR. 5111. In Texas Turfgrass Research Reports, ed. P. F. Colbaugh and S. F. Metz. Texas A & M University System, College Station, TX, 77843.

TABLE 13

Anther color on June 8, 1993 of 1992 NTEP bermudagrasses planted at TAES-Dallas.

| Entry | Anther color |
|---|---|
| Midfield | W[1] |
| Midlawn | PW |
| Tifgreen | W |
| STF-1 | P |
| Texturf 10 | P |
| Midiron | K |
| TDS-BM1 | W |
| Tifway | K |
| AZ common | K |
| JFHB-135 | — |

[1]Color is designated as P = purple, W = white, and K = pink. Entries that produced no flowers are indicated by '—'.
Morton, S. J. and M. C. Engelke. 1993. Bermudagrass entries in the National Turfgrass Evaluation program Trial at Dallas. PR. 5111. In Texas Turfgrass Research Reports, ed. P. F. Colbaugh and S. F. Metz. Texas A & M University System, College Station, TX, 77843.

TABLE 14

Percent shoot salt injury over six rating dates of 26 bermudagrasses included in the 1992 National Turfgrass Evaluation Program trial -TAES-Dallas.

| Vegetative Entry | 23 Oct | 27 Oct | 6 Nov | 13 Nov | 24 Nov | 13 Dec | TPI[1] |
|---|---|---|---|---|---|---|---|
| Tifway | 0 a | 37 a | 46 | 45 a | 71 | 68 a | 4 |
| Midlawn | 7 a | 47 | 43 a | 36 a | 75 | 71 a | 4 |
| Tifgreen | 0 a | 33 a | 30 a | 32 a | 56 a | 72 a | 6 |
| TDS-BM1 | 0 a | 32 a | 37 a | 37 a | 66 a | 73 a | 6 |
| FHB-135 | 6 a | 33 a | 32 a | 33 a | 62 a | 75 a | 6 |
| Midfield | 0 a | 47 | 50 | 52 | 76 | 80 | 1 |
| Ariz.Com | 0 a | 43 | 41 a | 47 | 86 | 83 | 2 |
| Midiron | 37 | 72 | 52 | 51 | 81 | 84 | 0 |
| Texturf 10 | 12 | 48 | 55 | 53 | 85 | 88 | 0 |
| STF-1 | 0 a | 32 a | 46 | 43 a | 77 | 93 | 3 |
| MSD entry[2] | 9 | 13 | 16 | 14 | 11 | 10 | |

[1]TPI = turf performance index, which was the number of times an entry occurred in the top statistical group.
[2]MSD entry - minimum significant difference between entry means for comparison within a column, which is based on the Waller-Duncan k-ratio t-test (K-ratio = 100). Means in the top statistical group are designated by an 'a'.
Marcum, K. B., M. C. Engelke, S. J. Morton, and C. Dayton. 1993. Salinity tolerances of selected bermudagrass and zoysiagrass genotypes. In Texas Turfgrass Research Reports, ed. P. F. Colbaugh and S. F. Metz. PR-5140. Texas A & M University System, College Station, TX, 77843.

TABLE 15

Pink snow mold tolerance during winter 1993–4 for the 1992 NTEP bermudagrasses planted at TAES-Dallas.

| Entry | Pink Snow mold %[1] 7 Mar 1994 |
|---|---|
| AZ common | 98 a |
| FHB-135 | 75 |
| Midfield | 82 a |
| Midiron | 94 a |
| Midlawn | 73 |
| STF-1 | 83 a |
| TDS-BM1 | 77 |
| Texturf 10 | 98 a |
| Tifgreen | 89 a |
| Tifway | 92 a |
| MSD entry[2] | 21 |

[1]Percentage is area of the plot without snow mold injury.
[2]MSD entry is the minimum significant difference between the entry means, which is based on the Waller-Duncan k-ratio t test (k-ratio = 100). 'ns' indicates that no statistical difference occurred between entry means. Means in the top statistical group are indicated by 'a'.
Morton, S. J. and M. C. Engelke. 1994. 1994 Update for the National Turfgrass Evaluation Program (NTEP) Trial at TAES-Dallas: 1992 Bermudagrass Trial. PR. 5240. In Texas Turfgrass Research Reports, ed. M. C. Engelke. Texas A & M University System, College Station, TX, 77843.

DETAILED SUMMARY OF DNA FINGERPRINT ANALYSIS

Takefumi Omura of Japan Turfgrass Inc. performed the DNA fingerprint analysis. The bermudagrass DNA fingerprints were TDS-BM1, Tifgreen, and Tifway. The DNA fingerprints were produced by extractions from the leaf tissue of the vegetatively propagated clones. The results of the DNA fingerprint analysis are summarized:

TDS-BM1 shows a distinctly different DNA from Tifgreen using RAPD analysis using a single primer of an arbitral oligonucleotide referred to as JAP 29 (FIG. 1) or JAP 26 (FIG. 2). Both TDS-BM1 and Tifgreen may be distinguished from Tifway using a single primer of an arbitral oligonucleotide referred to as JAP 26 (FIG. 2) and JAP 25 or JAP 27 (FIG. 3).

REFERENCES

National Bermudagrass Test-1992. Progress Report 1992. National Turfgrass Evaluation Program. USDA-ARS, Beltsville Agric. Research Ctr. Beltsville, Md. 20705.

National Bermudagrass Test-1992. Progress Report 1993. National Turfgrass Evaluation Program. USDA-ARS, Beltsville Agric. Research Ctr. Beltsville, Md. 20705.

I claim:

1. A new and distinct cultivar of bermudagrass plant, substantially as herein illustrated and described, characterized particularly by rapid vegetative establishment, superior shade tolerance, distinct DNA fingerprint; diminutive growth pattern, and white anthers.

* * * * *

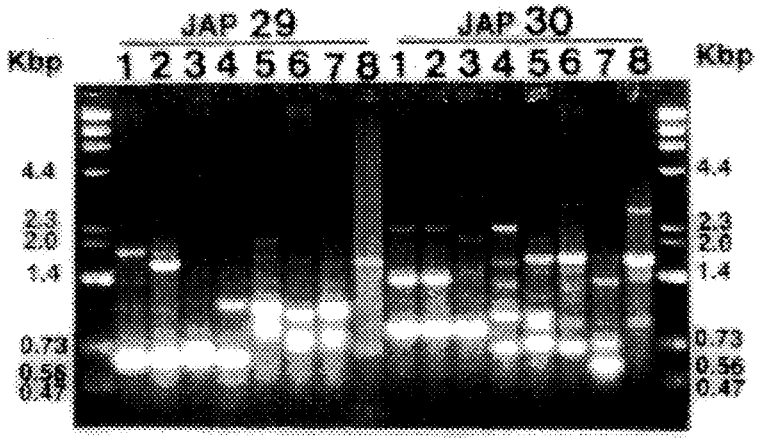

Fig. Comparison of RAPD patterns of cultivars within Bermudagrass or Baffalograss using single short primers of arbitral oligonucleotides.
1 : Bermudagrass cv. TDS-BM-1, 2 : Hybrid bermudagrass cv. Tifgreen, 3 : Hybrid bermudagrass cv. Tifway, 4 : Common bermudagrass,

Figure 1.

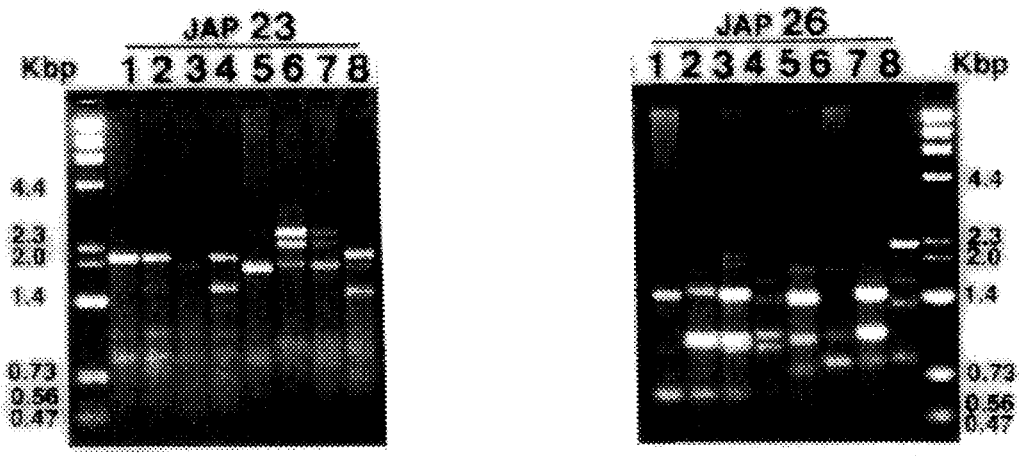

Fig. Comparison of RAPD patterns of cultivars within Bermudagrass or Baffalograss using single short primers of arbitral oligonucleotides.
1 : Bermudagrass cv. TDS-BM-1, 2 : Hybrid bermudagrass cv. Tifgreen, 3 : Hybrid bermudagrass cv. Tifway, 4 : Common bermudagrass,

Figure 2.

Fig. Comparison of RAPD patterns of cultivars within Bermudagrass or Baffalograss using single short primers of arbitral oligonucleotides.
1 : Bermudagrass cv. TDS-BM-1, 2 : Hybrid bermudagrass cv. Tifgreen, 3 : Hybrid bermudagrass cv. Tifway, 4 : Common bermudagrass,